United States Patent
Seeley et al.

(10) Patent No.: US 10,355,438 B2
(45) Date of Patent: *Jul. 16, 2019

(54) IMPLANTABLE MEDICAL DEVICES INCLUDING ELONGATED CONDUCTOR BODIES THAT FACILITATE DEVICE AND LEAD CONFIGURATION VARIANTS

(71) Applicant: MEDTRONIC, INC., Minneapolis, MN (US)

(72) Inventors: Dale F. Seeley, Spring Park, MN (US); Michael T. Hegland, Mounds View, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/041,798

(22) Filed: Jul. 22, 2018

(65) Prior Publication Data

US 2018/0331483 A1    Nov. 15, 2018

Related U.S. Application Data

(60) Division of application No. 15/799,515, filed on Oct. 31, 2017, now Pat. No. 10,038,294, which is a
(Continued)

(51) Int. Cl.
*A61N 1/37* (2006.01)
*H01R 43/20* (2006.01)
(Continued)

(52) U.S. Cl.
CPC .......... *H01R 43/20* (2013.01); *A61N 1/3752* (2013.01); *A61N 1/3754* (2013.01);
(Continued)

(58) Field of Classification Search
CPC .. A61N 1/3752; A61N 1/3754; H01R 13/504; H01R 2107/00; H01R 2201/12; H01R 24/58
See application file for complete search history.

(56) References Cited

U.S. PATENT DOCUMENTS 9,108,067 B2 *   8/2015   Seeley ................ A61N 1/3752

* cited by examiner

*Primary Examiner* — Amanda K Hulbert
(74) *Attorney, Agent, or Firm* — Withers & Keys, LLC

(57) ABSTRACT

Implantable medical devices include elongated conductor bodies and related features including an attachment to the medical device at one end and a connector that receives a medical lead at the other end. The connector may have various features such as a modular design whereby the connector is constructed from a series of stacked contact modules. Other features of the connector include electrical contacts that are relatively thin conductors or the order of 0.040 inches or less and that may include radial protrusions to establish contact with the electrical connectors of the lead. Furthermore, electrical contacts may be mounted within the connector in a floating manner so that radial movement of the electrical contact may occur during lead insertion. Additional features include a feedthrough where conductors exposed beyond a housing of the implantable medical device make direct electrical connection to conductors present within the elongated body.

10 Claims, 14 Drawing Sheets

Related U.S. Application Data division of application No. 15/162,562, filed on May 23, 2016, now Pat. No. 9,819,135, which is a continuation of application No. 14/828,495, filed on Aug. 17, 2015, now Pat. No. 9,345,896, which is a division of application No. 14/500,569, filed on Sep. 29, 2014, now Pat. No. 9,108,067, which is a division of application No. 14/256,955, filed on Apr. 19, 2014, now Pat. No. 8,849,405, which is a division of application No. 12/892,004, filed on Sep. 28, 2010, now Pat. No. 8,712,527.

(60) Provisional application No. 61/256,548, filed on Oct. 30, 2009.

(51) Int. Cl.
*A61N 1/375* (2006.01)
*H01R 13/504* (2006.01)
*H01R 24/58* (2011.01)
*H01R 43/00* (2006.01)
*H01R 107/00* (2006.01)

(52) U.S. Cl.
CPC ........... *H01R 13/504* (2013.01); *H01R 24/58* (2013.01); *H01R 43/005* (2013.01); *H01R 2107/00* (2013.01); *H01R 2201/12* (2013.01)

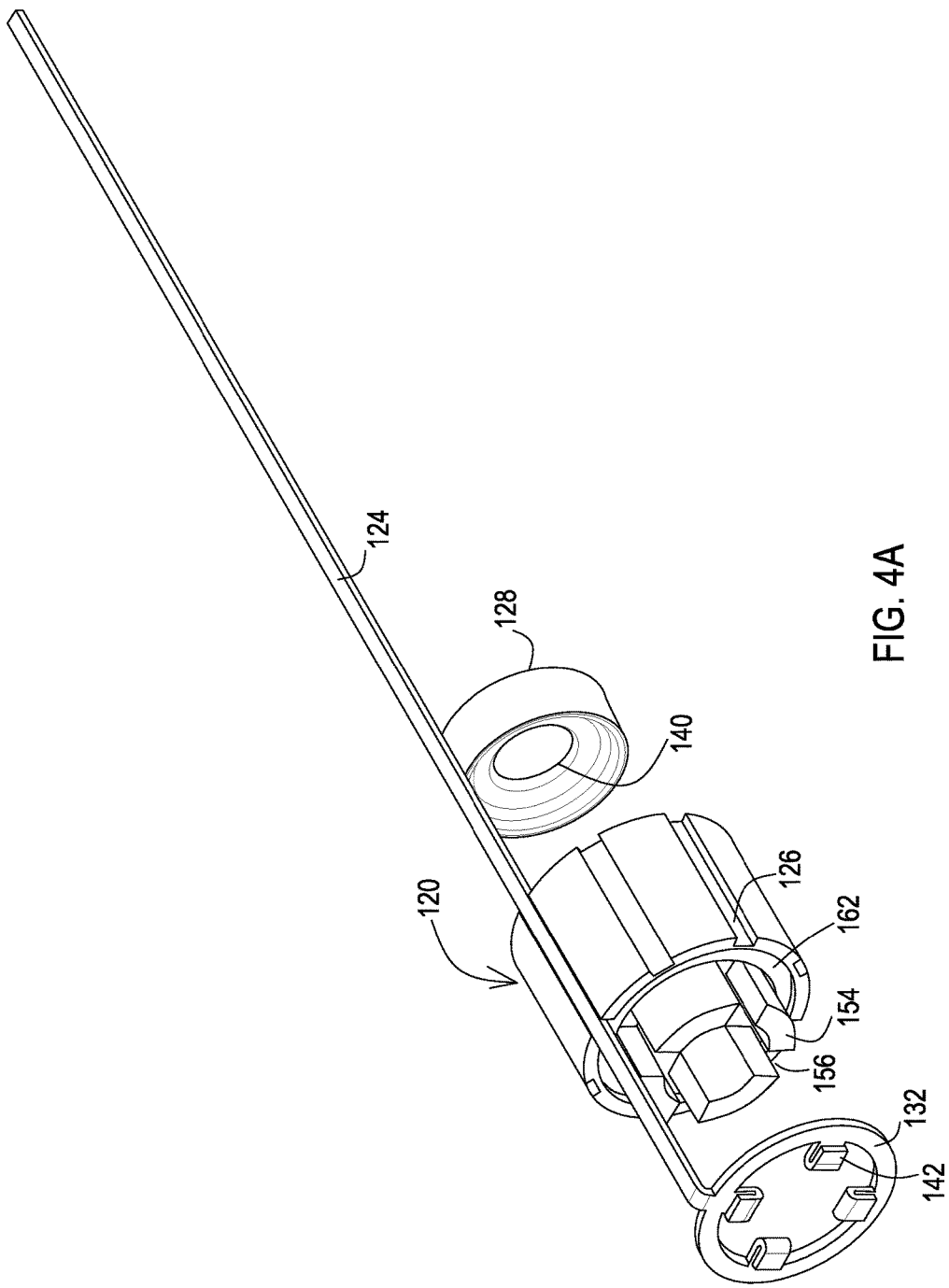

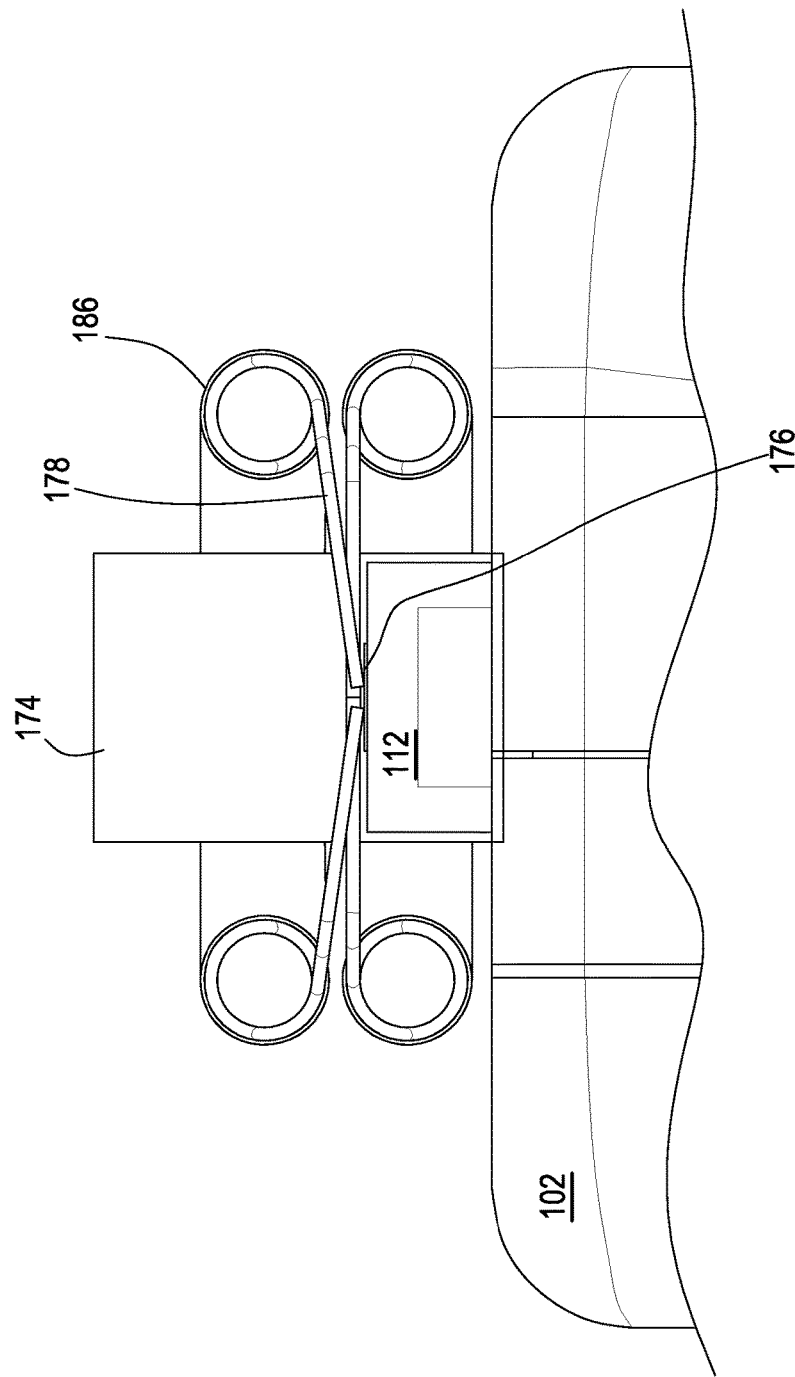

IMPLANTABLE MEDICAL DEVICES INCLUDING ELONGATED CONDUCTOR BODIES THAT FACILITATE DEVICE AND LEAD CONFIGURATION VARIANTS

RELATED APPLICATIONS

The present application is a divisional of U.S. Pat. No. 10,038,294 filed on Oct. 31, 2017, which is a divisional of U.S. Pat. No. 9,819,135 filed on May 23, 2016, which is a continuation of U.S. Pat. No. 9,345,896 filed on Aug. 17, 2015, which is a divisional of U.S. Pat. No. 9,108,067 filed on Sep. 29, 2014, which is a divisional of U.S. Pat. No. 8,849,405 filed on Apr. 19, 2014, which is a divisional of U.S. Pat. No. 8,712,527 filed on Sep. 28, 2010, which claims priority to U.S. Provisional Application 61/256,548, entitled IMPLANTABLE MEDICAL DEVICES INCLUDING ELONGATED CONDUCTOR BODIES THAT FACILITATE DEVICE AND LEAD CONFIGURATION VARIANTS, filed on Oct. 30, 2009, which is incorporated by reference herein

TECHNICAL FIELD

Embodiments relate to implantable medical devices. More particularly, embodiments relate to implantable medical devices that include elongated conductor bodies that facilitate connector configuration variants of leads and devices.

BACKGROUND

Implantable medical devices (IMD) such as cardiac and neural stimulators utilize circuitry within an enclosure to generate electrical stimulation pulses. The circuitry is electrically linked to contacts within a header that is attached to the enclosure by a set of conductive pins known as a feedthrough. The implantable medical leads are physically connected to the header and include connectors on a proximal end that engage the electrical connectors within the header. The implantable medical leads also include electrodes near a distal end with the conductors carrying the stimulation pulses from the connectors to the electrodes.

The number of leads needed for a particular therapy and corresponding IMD may vary as may the number of electrical connections per lead. Hence the design of the header must also vary to accommodate the feedthrough of a given device and the number of leads and lead connectors that are necessary. For example, 24 electrodes may be configured in numerous ways for a device and therapy. One neurostimulator may drive eight electrodes per lead for three leads. Another neurostimulator may drive eight electrodes per lead for two leads and four electrodes per lead for two additional leads. Yet another neurostimulator may drive twelve electrodes per lead for two leads.

In these variations, entirely different header designs are used. Such header designs conventionally use ribbon bonds and lead frames as the interconnection between the feedthrough and the pressure contact, often a canted-coil spring, in the header. The development and resulting design for the ribbon bonds, lead frames, and related feedthrough become very specific for each IMD model and related leads and do not directly transfer to other IMD models and leads. Furthermore, the manufacturing processes to construct the headers having distinct designs for the different IMD models can be challenging. Thus, the development and manufacturing processes for headers being designed for each of the IMD models is burdensome.

In addition to the burdens of development and manufacturing, the designs that involve a relatively large number of pressure contacts in the header per lead can be troublesome. Typically, the pressure contacts such as the canted-coil springs can necessitate a large insertion force when numerous pressure contacts are needed for a particular lead. The insertion force may exceed the capabilities of the lead to maintain physical integrity. Lead insertion may be difficult and lead damage may also occur during insertion.

Additionally, because the header is rigidly attached to the IMD enclosure, the insertion of each lead requires some degree of manipulation of the IMD to correctly align the lead with the lead passageway of the header. This becomes progressively more burdensome as leads are sequentially inserted and begin to crowd and clutter the area immediately adjacent the entryway to the header.

Furthermore, the size of the header is directly related to the connector spacing on the lead, or lead pitch. As the number of electrodes per lead increases the header size increases, and the increase may be significant due to the relatively large size of conventional electrical contacts such as the canted-coil springs. This relationship contradicts the efforts to develop smaller IMDs which are often more desirable for implantation.

SUMMARY

Embodiments address issues such as these and others by providing various features for one or more elongated conductor bodies installed on an IMD. For instance, in some embodiments, the elongated body may have a connector on a distal end where that connector may be constructed of individual modules that may be stacked together to form a passageway for the lead within the connector. The modules may have a particular design for a lead passageway that is replicated from one connector design to the next to produce the desired number of lead passageways for a particular IMD and therapy. Electrical contacts may be provided between various modules so that the number and placement of the electrical contacts may be easily selected and varied from one connector design to the next.

In some embodiments, the electrical contacts of the connectors may have a design that allows several modules to be stacked while retaining a relatively small contact spacing known as pitch and while retaining a relatively small insertion force requirement. The electrical contacts may be in the form of a contact conductor that surrounds the lead passageway while having a relatively small thickness in the axial dimension of the lead passageway, such as on the order of 0.040 inches or less. The electrical contacts may include multiple radial protrusions spaced about the electrical contact. These radial protrusions may engage the electrical connectors on a lead being inserted into the lead passageway of the connector.

Furthermore, in some embodiments, the electrical contacts may float within the lead passageways of the connectors. The ability to float with subtle radial movements during insertion better aligns the contact to the lead connectors. As the proximal end of the lead and the series of lead connectors on the proximal end may have concentricity imperfections, the floating electrical contact further lessens insertion force requirements.

In some embodiments, the one or more elongated bodies may connect to the IMD enclosure by providing a boot that receives a proximal end of each of the one or more elongated bodies and that surrounds the feedthrough of the IMD. Electrical conductors introduced into the boot via the feedthrough provide a direct connection to the electrical conductors in the elongated body to avoid intervening conductors and related connections.

DESCRIPTION OF THE DRAWINGS

FIG. 4A shows an exploded perspective view of a contact module, electrical contact, and contact isolator of an embodiment of the connector.

FIG. 13 shows a back view of the feedthrough and related conductors with the boot and cable sleeves omitted for clarity.

DETAILED DESCRIPTION

Embodiments provide for implantable medical devices that include a housing, an elongated body that extends from a connection to the housing, and a connector attached to an end of the elongated body that receives a medical lead. This combination of the elongated body and the connector allows for device and lead configuration variants. Embodiments of the connector may be modular whereby contact modules of a particular design may be stacked to achieve the number of electrical contacts that are necessary for a given device and lead configuration. Furthermore, the number of elongated bodies that extend from a connection to the housing may vary to accommodate the number of leads that are necessary for a given device configuration.

Embodiments of the connection of the elongated body to the housing may simplify connectivity relative to a conventional header design by providing for direct electrical connections between electrical conductors of the elongated body and the feedthrough conductors of the device. The feedthrough conductors may be exposed within a boot that provides the attachment of the elongated body to the device to achieve electrical connection to the electrical conductors of the elongated body, and ultimately to the electrical contacts of the connector.

Embodiments of the connectors may allow for a relatively large number of electrical connections for a given lead by providing relatively thin electrical contacts, on the order of 0.040 inches or less in the axial dimension in addition to providing the connector at the end of the elongated body that extends from a connection to the housing. The thin nature of the electrical contacts reduces the axial space needed for a large number of electrical connections to a lead.

Embodiments of the connectors may allow for a relatively large number of electrical connections for a given lead by reducing scraping forces that occur during lead insertion. The reduction may be provided by the thin and flexible nature of radial protrusions of some embodiments of the electrical contacts within the connector. The reduction may be additionally or alternatively provided by allowing the electrical contact to radially float within the connector to better align with concentricity variations of the lead.

Figure 1:
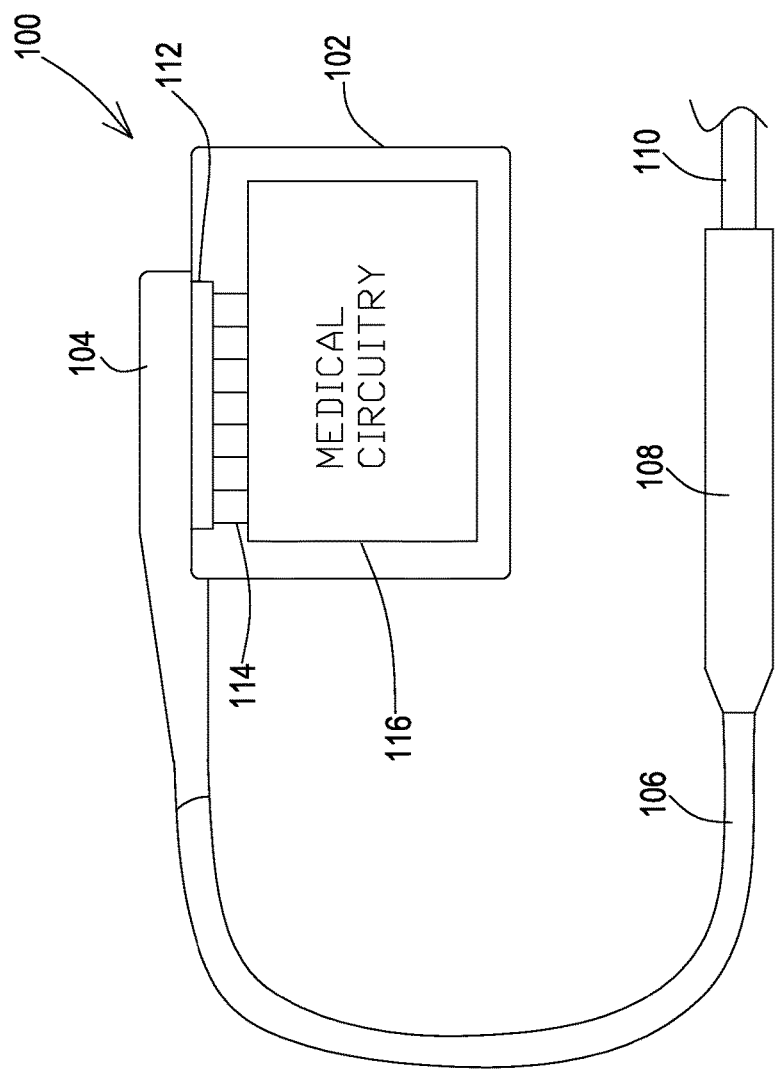
FIG. 1 shows an implantable medical device including an embodiment of a harness that includes a boot, elongated body, and connector.

FIG. 1 shows one example of an implantable medical device (IMD) 100. The IMD 100 includes a housing 102 that encloses medical circuitry 116 that is used to provide the medical function of the IMD 100. The medical circuitry 116 may include various components such as one or more batteries, controllers, pulse generators, and the like. The housing 102 is typically constructed of biocompatible materials such as various grades of titanium. The IMD 100 is typically implanted at a site within a patient's body or may be mounted externally of the body in some instances.

The IMD 100 includes a feedthrough 112 that exposes electrical conductors externally of the housing 102. The electrical conductors may be the ends of the electrical pins 114 that exit the medical circuitry 116. Alternatively, the electrical conductors exposed by the feedthrough 112 may be electrical contact pads that are electrically connected to the pins 114.

The IMD 100 also includes a boot 104 that is mounted to the housing 102 in a sealed relationship that resists body fluids from penetrating into the junction to the housing 102. The boot 104 receives the electrical conductors exposed beyond the housing 102 via the feedthrough 112. The boot 104 also receives a proximal end of one or more elongated bodies 106.

The elongated body 106 may be flexible like a conventional medical lead and is attached at a distal end to a connector 108 that receives a medical lead 110. In some embodiments, the length of the elongated body 106 may be significantly less than that of a conventional medical lead so that the connector 108 is in close proximity to the housing 102. In such a case, the medical leads 110 may be implanted in the normal manner with the proximal end of the medical lead 110 inserted into the connector 108 rather than being inserted into a conventional header.

The connector 108 may include various structures for fixing the position of the medical lead 110, such as set screw blocks and the like. The set screw block or other manner of fixing the medical lead 110 may be located within a contact module of the connector 108, for instance the most distal contact module. The medical lead 110 that is inserted into the connector 108 has electrical connectors on the proximal end, electrodes on a distal end, and conductors that interconnect the two.

The connector 108 includes electrical contacts, discussed in more detail below, that contact corresponding electrical connections of the medical lead 110. These electrical contacts are also in electrical communication with corresponding electrical conductors within the elongated body 106 and carry electrical signals between the electrical connections of the lead 106 and the electrical conductors of the elongated body 106. The electrical conductors of the elongated body 106 carry the electrical signals between the feedthrough conductors and the electrical contacts of the connector 108.

Figure 2:
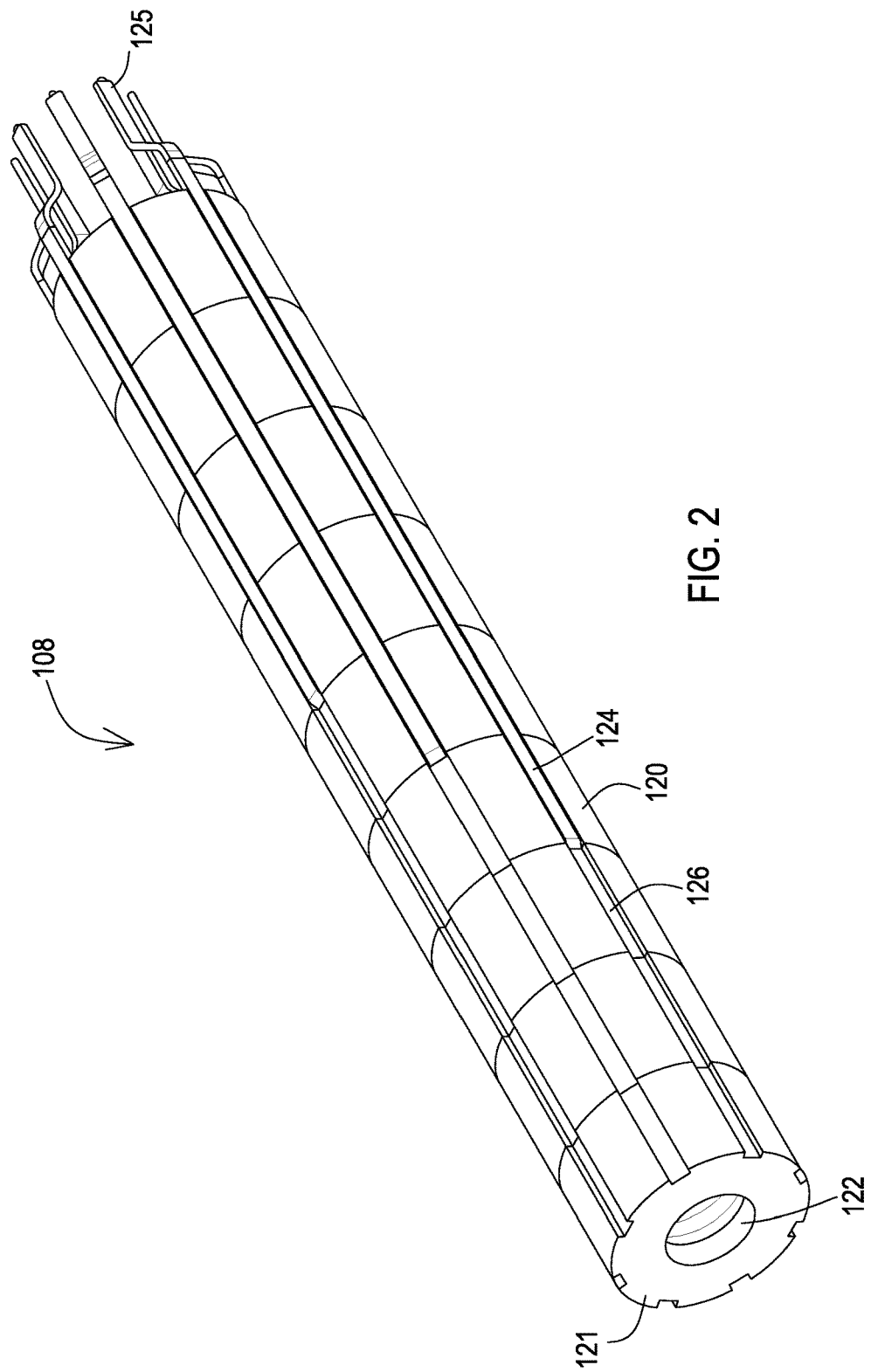
FIG. 2 shows a perspective view of an embodiment of the connector of the harness.

FIG. 2 provides a view of the internal components of one embodiment of the connector 108. These components include a series of contact modules 120 that are stacked to create the axial dimension of the connector 108. It should be noted that the contact modules 120 being stacked refers to being positioned immediately adjacently to one another without regard to horizontal or vertical orientation of the stack. The contact modules 120 may be constructed of various non-conductive materials that ultimately provide a rigid structure such as injection molded plastics. The contact modules 120 house other components such as the electrical contacts of the connector 108. Once these components are installed relative to the contact modules 120, the contact modules 120 may be stacked together in the length needed for a particular device and lead configuration. The contact modules 120 may also then be fused by a process such as an ultrasonic weld or adhesive bonding to create one rigid and sealed connector body. The stacking and sealing may be done by holding each module relative to a common reference point to improve the dimensional tolerance of the final assembly.

FIG. 2 also shows additional features. A lead passageway 122 is established by each of the contact modules 120 and ultimately the connector 108. Additionally, each contact module 120 includes a set of circumferentially spaced channels 126.

Electrical contacts are present within the connector 108 and are discussed in more detail below with reference to FIGS. 3-7. Each of these electrical contacts includes an extension 124 that exits from within the connector 108 and rests within one of the channels 126 that is dedicated to that particular extension 124. The extension has a length that matches the distance from the electrical contact to the proximal end of the connector 108 so that while each electrical contact has a different distance to the proximal end, each extension 124 ends at the same point in the axial direction.

In this example, bridging conductors 125 are either formed integrally at the ends of the extensions 124 or may be separate conductors attached to the ends of the extensions 124 such as by a friction fitting or a weld. However, it will be appreciated that the bridging conductors 125 may be integral to the extensions 124. The bridging conductors 125 electrically connect the extensions 124 to corresponding connectors within the elongated body 106. These connectors and conductors within the elongated body 106 are discussed in more detail below with reference to FIG. 7.

While the contact modules 120 are visible in FIG. 2, the series of contact modules 120 forming the connector 108 may be encapsulated in a polymer shell. This may be beneficial for embodiments where the channels 126 are otherwise exposed. The polymer shell may seal the channels 126 so that the extensions 124 are not exposed to ambient conditions about the connector 108, which prevents conductive bodily fluids from short circuiting the extensions 124 that originate from different electrical contacts within the connector 108. As an alternative to, or in addition to the polymer shell, the extensions 124 may be coated with a non-conductive material, such as polytetrafluoroethylene (PTFE) or ethylene tetrafluoroethylene (ETFE) to prevent shorting circuiting between extensions 124.

The connector 108 also includes an end cap module 121. This module 121 terminates the lead passageway 122 by providing a blunt distal end to the connector 108. The connector 108 is further discussed below with reference to FIGS. 6 and 7.

Figure 3:
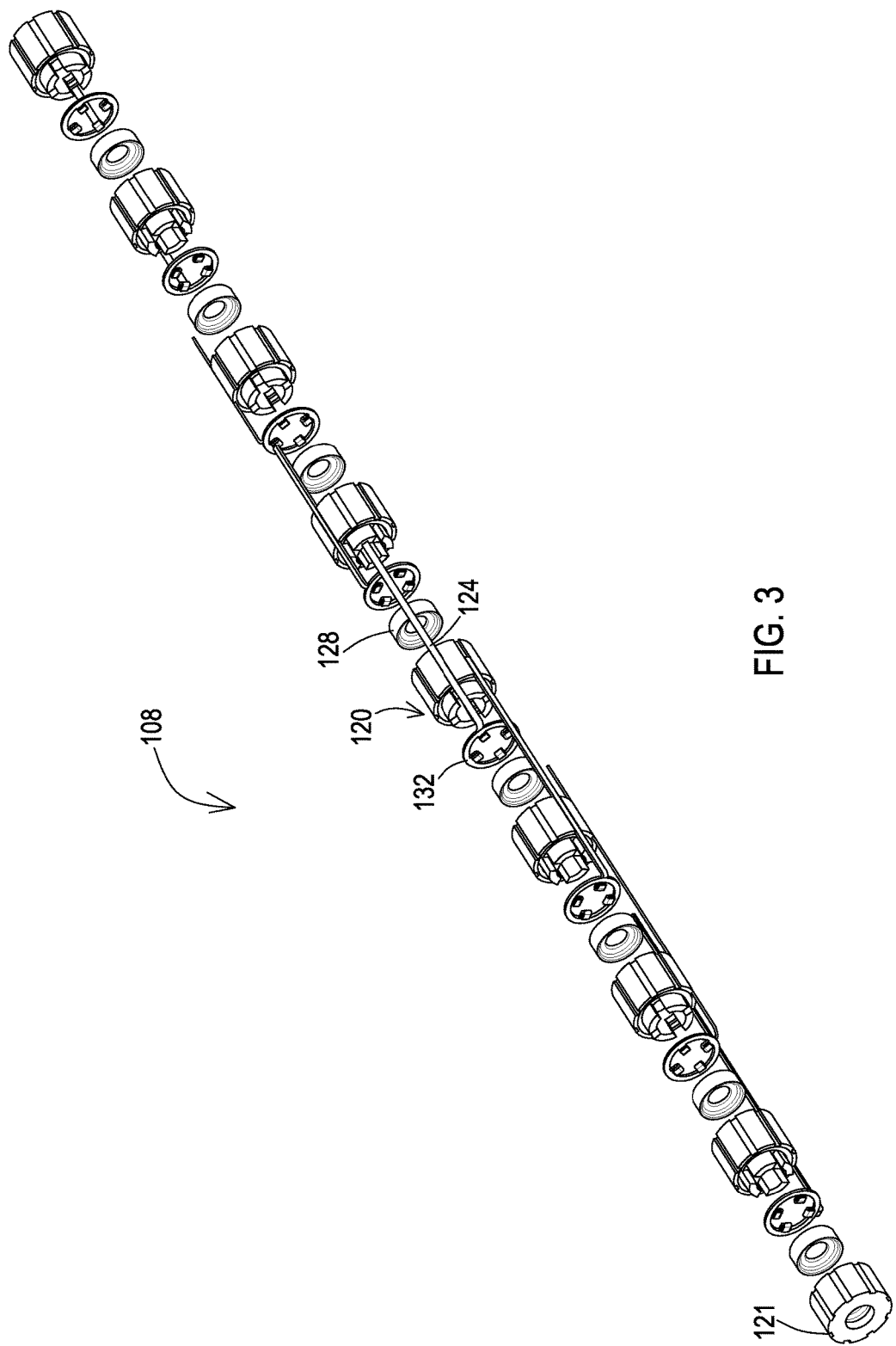
FIG. 3 shows an exploded perspective view of contact modules of an embodiment of the connector.

FIG. 3 shows an exploded view of the connector 108 and each of the components of this particular embodiment. The lead passageway 122 of each contact module 120 receives a corresponding contact isolator 128. The lead passageway 122 of each contact module 120 also receives a corresponding electrical contact 132. The contact isolator 128 is present to provide a sealing engagement to the insulator of the lead body that is present between electrical connectors of the lead 110. This sealing engagement provides a degree of isolation between the series of electrical contacts 132 of the connector 108 so that the distinct electrical pathways are less likely to become electrically shorted by conductive bodily fluids that are present about the connector 108.

FIG. 4A shows the contact module 120, contact isolator 128, and electrical contact 132 according to this particular embodiment. The contact module 120 has a set of axial extensions 154 that upon assembly enter the lead passageway 122 of the adjacent contact module 120. This engagement of the axial extensions 154 to the lead passageway 122 aids in properly aligning the contact modules 120 and also provides structural support for the connector structure 108 by stabilizing the position of one contact module 120 relative to an adjacent one both before and after fusing of the contact modules 120.

In this embodiment, the contact module 120 may have various features that relate to the electrical contact 132. The axial extensions 154 are arranged circumferentially and define spaces 156 that accommodate the electrical contact 132. The electrical contact 132 of this embodiment is a thin conductive ring with radial protrusions 142. These radial protrusions 142 reside within the spaces 156 as the electrical contact 132 is placed about the axial extensions 154 to surround the lead passageway. The contact module 120 may include a recess 162 that allows the electrical contact 132 to rest in place between adjacent contact modules. The recess 162 may join with the specific channel that receives the axial extension 124 of the electrical contact 132 to allow the axial extension 124 to exit from the interior of the contact module 120.

The electrical contact 132 of this particular embodiment utilizes the radial protrusions 142 to establish physical and electrical contact with the electrical connectors of the lead 110. In the example shown, there are four radial protrusions, each having a U shape with the bend of the U shape providing the contact surface. This relatively small point of contact may be useful to lessen the scraping force that occurs during lead insertion. Furthermore, the radial protrusions may be provided with a degree of flexibility so that they may deflect slightly in the axial direction to further reduce scraping forces and to snugly engage the electrical connectors of the lead 110.

An additional feature of the electrical contact 132 relevant to lead insertion may be a radial floating relationship to the contact module 120. This radial floating relationship may be provided by having electrical contact 132 with an inner diameter that is greater than the outer diameter established by the axial protrusions 154. An outer diameter of the electrical contact 132 may be less than the outer diameter established by the recess 162. The spacing between axial extensions 154 of a set may be greater than the width of the radial protrusions 142. As a result of these size relationships, a degree of freedom in the radial direction is established for the electrical contact 132 that allows the electrical contact 132 to better accommodate concentricity imperfections in the lead 110 as it is being inserted.

The electrical contact 132 may be constructed of various conductive materials such as titanium, titanium alloys, MP35N, and the like. The electrical contacts may be of various sizes; however, a thickness ranging from 0.004 to 0.040 inches may have adequate structural integrity while offering the benefit of reduced scraping force. For the electrical contact 132 as shown, the thickness may range from 0.004 to 0.020 inches so that the resulting thickness of the radial protrusion ranges from 0.008 to 0.040 inches. Furthermore, the thin nature of the electrical contact may allow for a relatively small center-to-center spacing of electrical contacts known as lead pitch, such as 0.080 inches or less.

While the electrical contact 132 of a particular design is shown relative to the contact module 120, it will be appreciated that other electrical contact designs are also applicable to a connector constructed from a series of contact modules. Likewise, while a particular connector design employing a series of contact modules is shown, it will be appreciated that other connector designs including non-modular designs are also applicable for use of thin electrical contacts with radial protrusions.

Figure 4B:
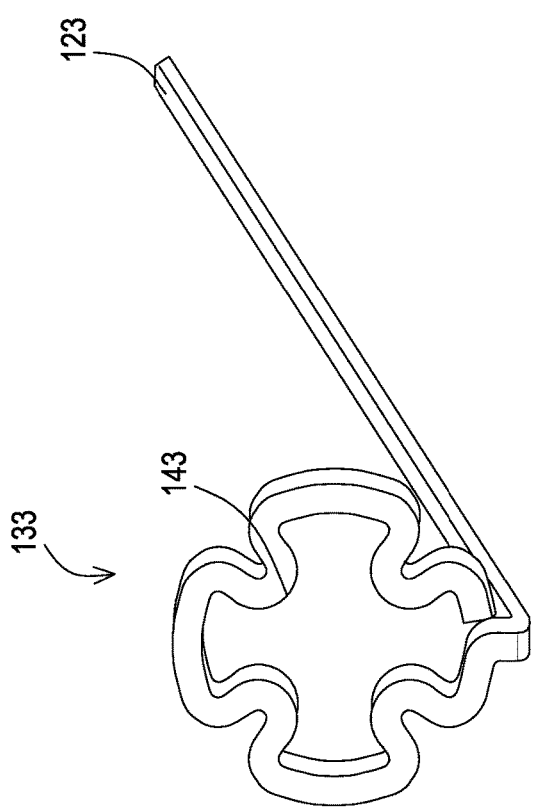
FIG. 4B shows an alternative electrical contact.

FIG. 4B shows an alternative electrical contact 133. This electrical contact 133 is a wireform that also is within and surrounds the lead passageway 122 and is contained by axial extensions of a contact module. The axial extensions that cooperate with the electrical contact 133 are shaped to fit the particular wireform shape, as opposed to having the shape shown in FIG. 4A. The wireform electrical contact 133 may be sized to float in the manner as the electrical contact of FIG. 4A. The wireform electrical contact 133 may also have a thickness in the axial direction on the order of 0.004 to 0.040 inches.

In this particular example, the wireform electrical contact 133 is in the shape of a shamrock and includes four radial protrusions 143 to establish points of contact on the electrical connector of the lead 110. However, it will be appreciated that other wireform shapes are applicable such as a triangular shape, diamond shape, and the like where small points of contact to the lead connector are established by the linear regions of the shape rather than by radial protrusions. The wireform electrical contact 133 also includes an extension 123 that may extend along a channel 126 until reaching the proximal end of the connector 108.

FIG. 4A also shows the contact isolator 128 which is positioned within the lead passageway 122 to form a seal at the point of contact with the contact modules 120. These contact isolators include an aperture 140 through which the lead 110 passes during insertion into the connector 108. The aperture 140 may have a diameter that is slightly less than that of the lead 110. Furthermore, the contact isolator 128 may be constructed of an elastic material such as silicone rubber so that the aperture expands during lead insertion and forms a tight seal against the lead body to reduce the likelihood of bodily fluids creating a conductive path from one electrical contact of one contact module to an electrical contact of an adjacent module.

The contact isolator 128 is elastic while the contact module 120 is rigid and thus the two types of components may be manufactured separately as shown. However, a co-injection molding process may instead be used to form the contact isolator 128 from an elastic material together with the contact module 120 from a rigid material together as one piece.

Figure 5:
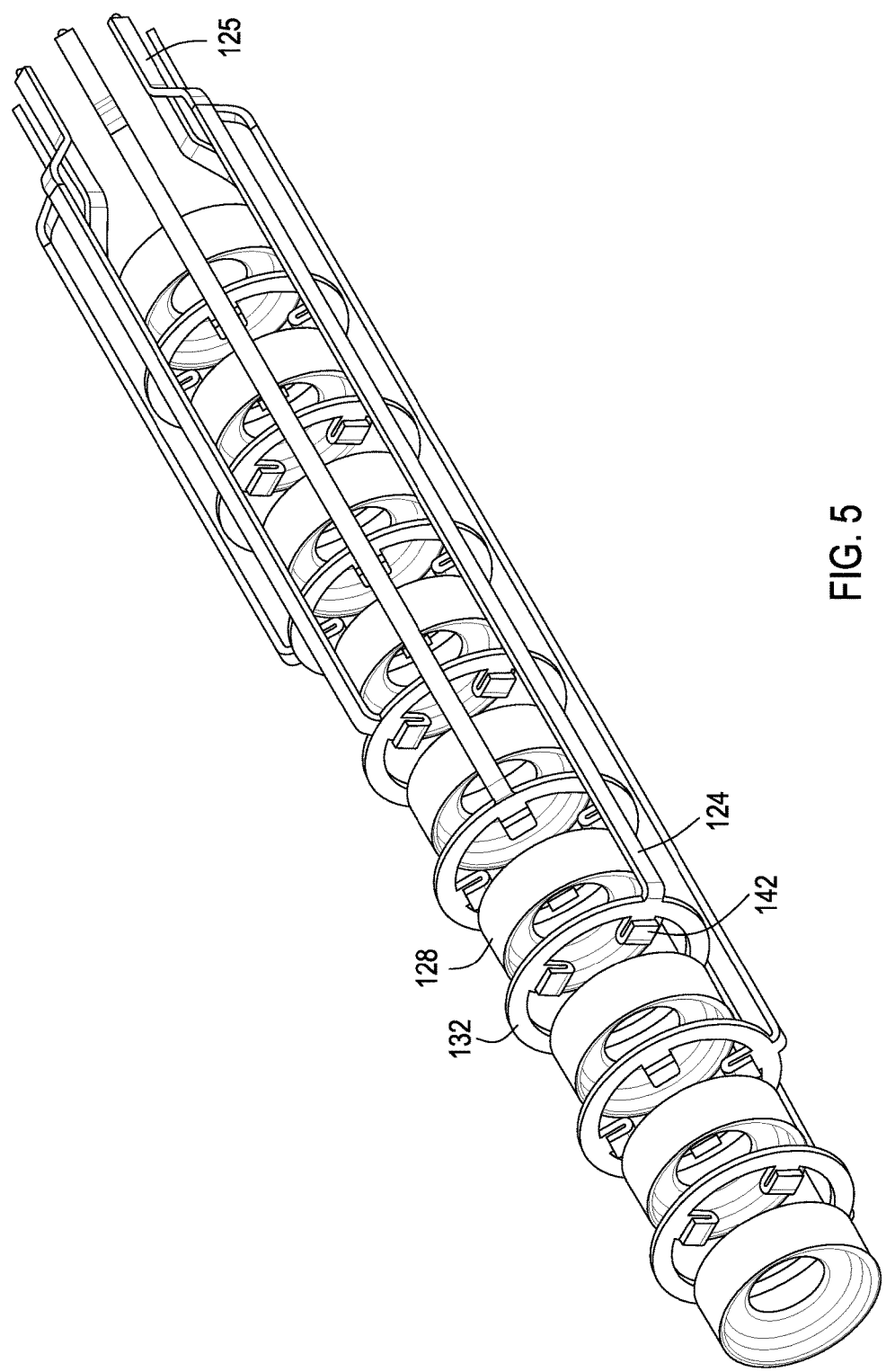
FIG. 5 shows a perspective view of an arrangement of electrical contacts and contact isolators with the contact modules being omitted for clarity.

FIG. 5 shows a view of the connector components but with the contact modules 120 omitted for clarity of illustration. This view illustrates the relative placement of the electrical contacts 132, extensions 124, bridging conductors 125, and contact isolators 128. Here it can be seen that each electrical contact 132 is axially between a pair of axially spaced contact isolators 128 on each side to provide a sealed space for each electrical contact 132. The differing lengths of the extensions 124 that result in the extensions terminating at the same point on the proximal end of the connector 108 can also be seen.

Figure 6:
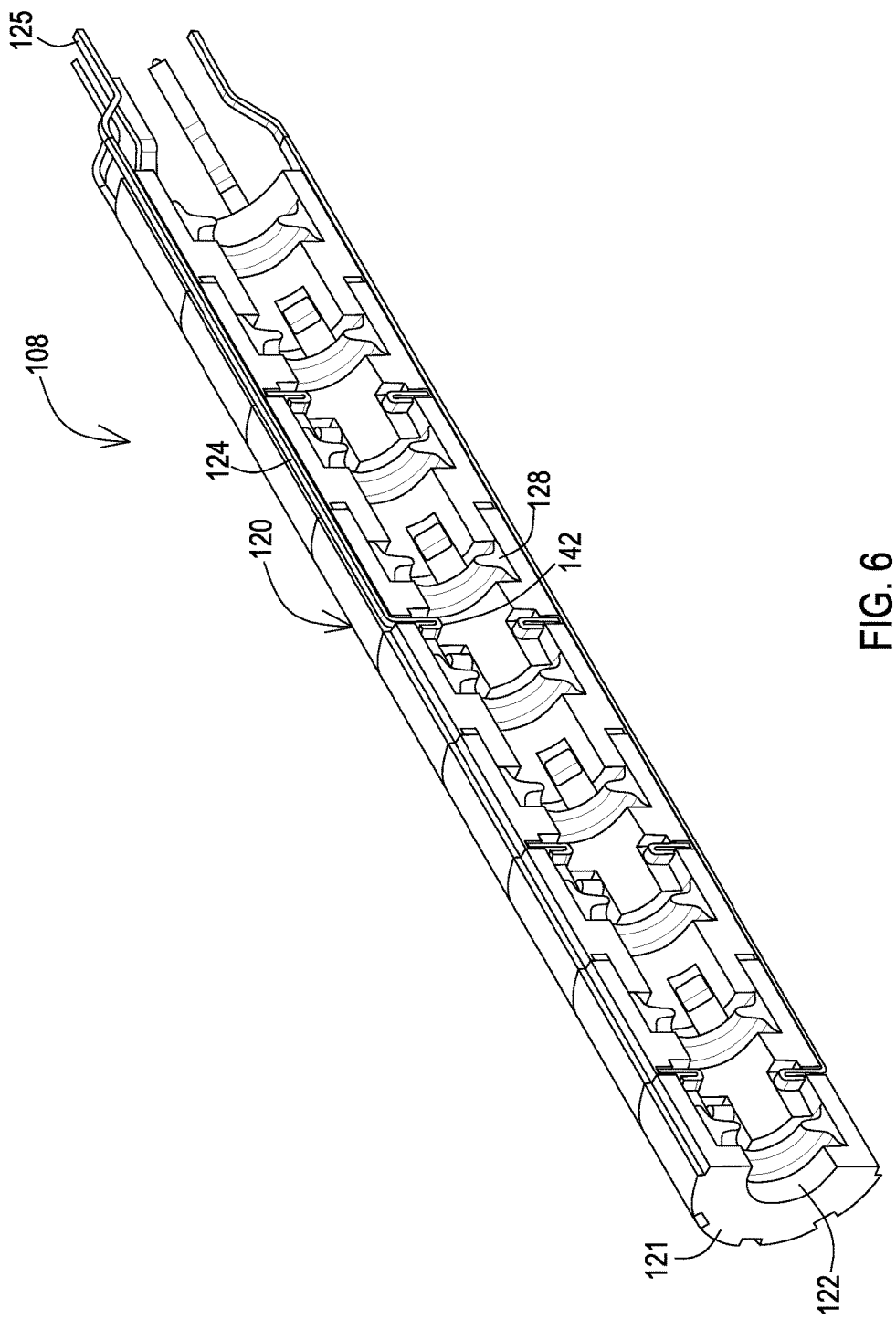
FIG. 6 shows a perspective cross-sectional view taken through an embodiment of a connector.
Figure 7:
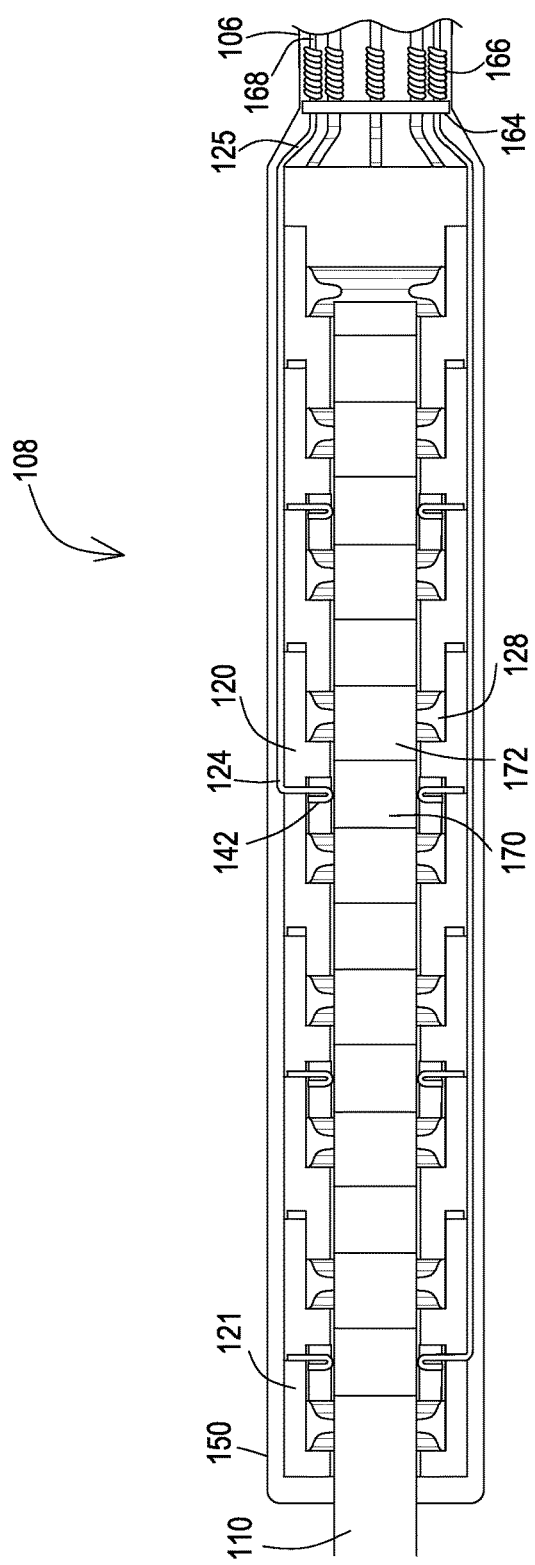
FIG. 7 shows a top view normal to the plane of the cross-section of FIG. 6 and with a medical lead being fully inserted into the connector.

FIG. 6 shows a cross-sectional perspective view of this example of a connector 108. FIG. 6 provides a reference for viewing FIG. 7. FIG. 7 is a top view of the connector 108 and includes the lead 110 in a fully inserted position.

FIG. 7 shows electrical connectors 170 of the lead 110. FIG. 7 also shows the insulator section 172 of the lead 110 that is positioned between electrical connectors. FIGS. 6 and 7 show the containment of the electrical contacts 132 and contact isolators 128 within the contact modules 120. It can be seen that the contact isolators 128 are positioned between an end of the axial extensions of one contact module and an inner abutment of an adjacent contact module.

FIGS. 6 and 7 show the presence of the radial protrusions 142 of the electrical contacts 132 relative to the lead passageway 122, and FIG. 7 shows the electrical connection of the radial protrusions 142 to the electrical connectors 170 of the lead 110. In this particular example, as shown in FIG. 4A, there are four radial protrusions 142 and corresponding spaces 156 defined by the axial protrusions 154, and these features shift by 45 degrees relative to the radial protrusions and spaces of adjacent electrical contacts and contact modules. As a result, the radial protrusions 142 are visible in the cross-section only at every other contact module 120. This shift allows the extension 124 of one electrical contact to have a dedicated channel 126 and be separated by 45 degrees from an extension 124 of an adjacent contact module 120 that lies within the next channel. It will be appreciated that the radial protrusions 142 may be at other angles as may the spacing from the axial extensions for those embodiments that include axial extensions, particularly where the number of radial protrusions 142 and/or the total number of electrical contacts 132 differ from the number shown.

FIG. 7 further shows the contact isolators 128 within the lead passageway 122 making physical contact with the insulator sections 172 of the lead 110. As discussed above, this contact establishes a seal on each side of each electrical contact to electrical connector pairing to reduce the likelihood of fluid conducting between adjacent electrical contacts.

FIGS. 6 and 7 further show the end cap module 121 which provides a blunt end to the connector 108. The end cap module 121 of this example omits the axial extensions 154 and the recess 162. As shown in FIG. 7, the end cap 121 as well as the remainder of the connector 108 may be encapsulated in a polymer layer 150 to further seal and stabilize the connector 108.

FIG. 7 further shows connectivity of the bridge conductors 125 to the conductors of the elongated body 106. In this particular example, the bridge conductors 125 pass through an end plate 164 that separates the elongated body 106 from the connector 108. The end plate 164 of this example includes a set of conductive coils 166, one for each bridge conductor 125. The bridge conductor 125 rests within the respective coil 166 where an interference fit may provide a snug physical and electrical connection and/or a weld may be done to establish a physical and electrical connection. Electrical conductors 168 within the elongated body 106 are attached to the conductive coils 166 either by a similar interference fit to the coils 166 or by other attachments such as a weld or other bond.

There may be various benefits for some embodiments having each extension 124 terminate via the bridge conductors 125 at the proximal end of the connector 108 where connection is made to the elongated body 106. For instance, the conductors 168 of the elongated body 106 may terminate at the end of the elongated body 106 rather than extending from the body and into the connector 108 which may simplify some aspects of construction of the connector 108. This may also simplify the electrical connection of the conductors 168 to the contacts 132 of the connector 108. This also allows the conductors 168 to be of an entirely different construction and type of material than the extensions 124 if desired, such as using coiled conductors 168 within a lumen of the elongated body 106 while using straight extensions 124.

While the example of FIGS. 1-7 has shown a single connector 108 with a single lead passageway 122 for a single lead 110, it will be appreciated that multiple leads can be accommodated. For instance, the boot 104 may provide a point of attachment of multiple elongated bodies with each elongated body providing a connector that receives at least one lead. As another example, the connector may have multiple lead passageways to thereby accept multiple leads.

Figure 8:
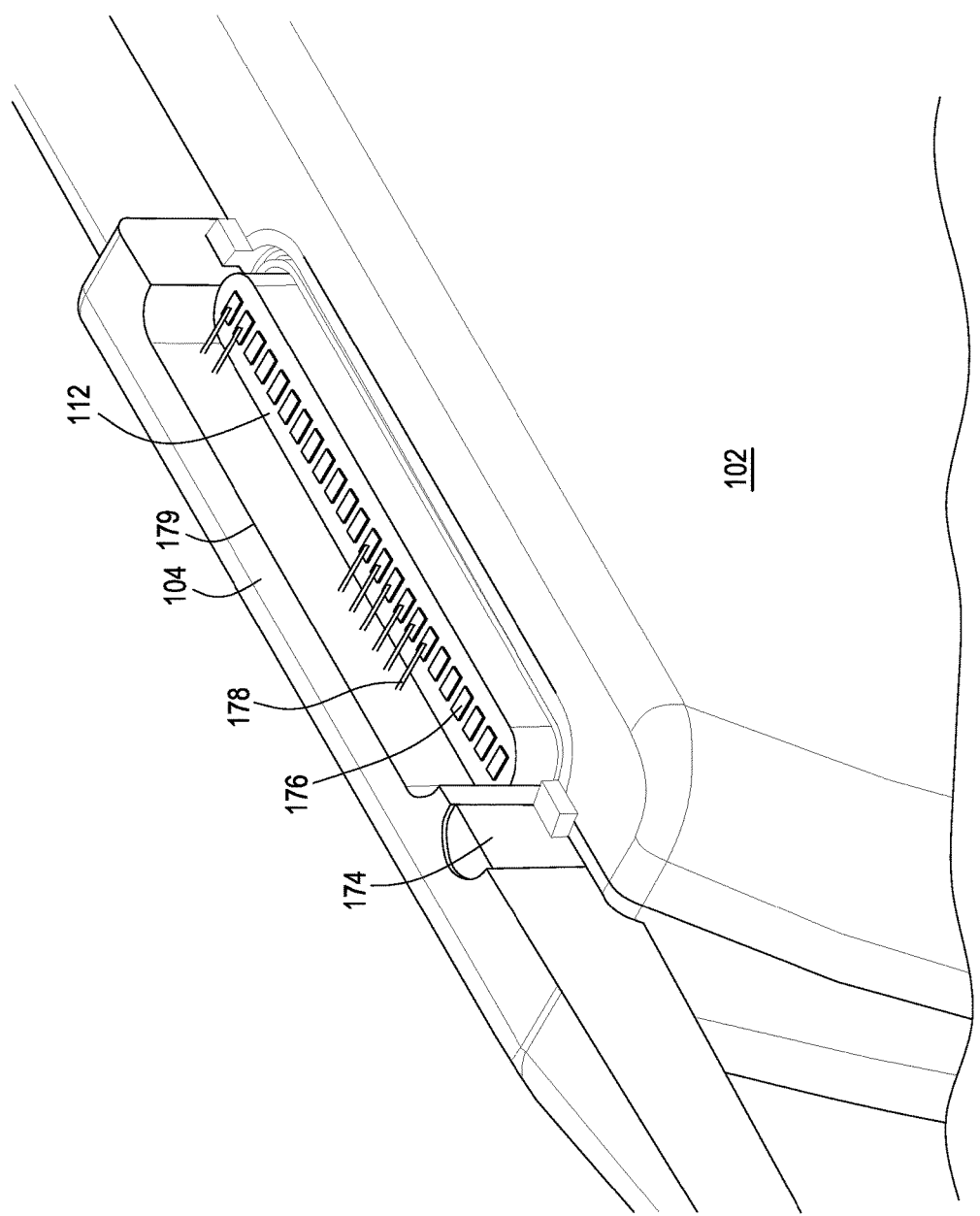
FIG. 8 shows a cross-sectional perspective view of one example of the boot positioned about a feedthrough of the implantable medical device.

FIG. 8 shows a cross-sectional perspective view of one example of the boot 104 for an example of the IMD 100. The boot 104 surrounds the feedthrough 112 that passes through the housing 102. The housing 102 may provide a mounting post 174 or other similar feature upon which the boot 104 may reside to be held in place about the feedthrough 112. The boot 104 may include an aperture 179 that exposes the feedthrough 112 for purposes of establishing electrical connections via welds between feedthrough conductors such as the electrical contact pads 176 of the feedthrough 112 and conductor portions 178 within the boot 104. The boot 104 may be encapsulated in a polymer once assembly is complete to seal the boot 104 including the connection of the conductor portions 178 to the contact pads 176. To the extent the electrical connections between conductor portions 178 and contact pads 176 are established before attachment of the boot 104, then the boot 104 may omit the aperture 179 and the encapsulation may be omitted.

In this particular view, only eight conductor portions 178 are shown. However, the feedthrough 112 may provide any number of contact pads 176 and in this example, 24 contact pads 176 are present to support up to 24 electrical contacts of one or more connectors 108. As can be seen, the conductor portions 178 occupy no more space axially than the contact pads 176 so that the boot 104 is sized to fit about the feedthrough 112 and occupy a relatively small amount of space on the housing 102 in comparison to a conventional header. As a result, the reduction in size of the housing 102 is not as limited by the size of the boot 104 as it would be limited by the size of a conventional header.

The boot 104 may be molded with the proximal end of the elongated body and related conductors in place so that the boot 104 holds the wiring in a proper orientation and with a proper spacing needed for assembly. As discussed below with reference to FIG. 9, the conductors of the elongated body that are present within the boot align with the feedthrough conductors such as the contact pads 176 so that physical and electrical attachment can be completed. The boot 104 being molded over the elongated body and conductors may facilitate that assembly process.

Figure 9:
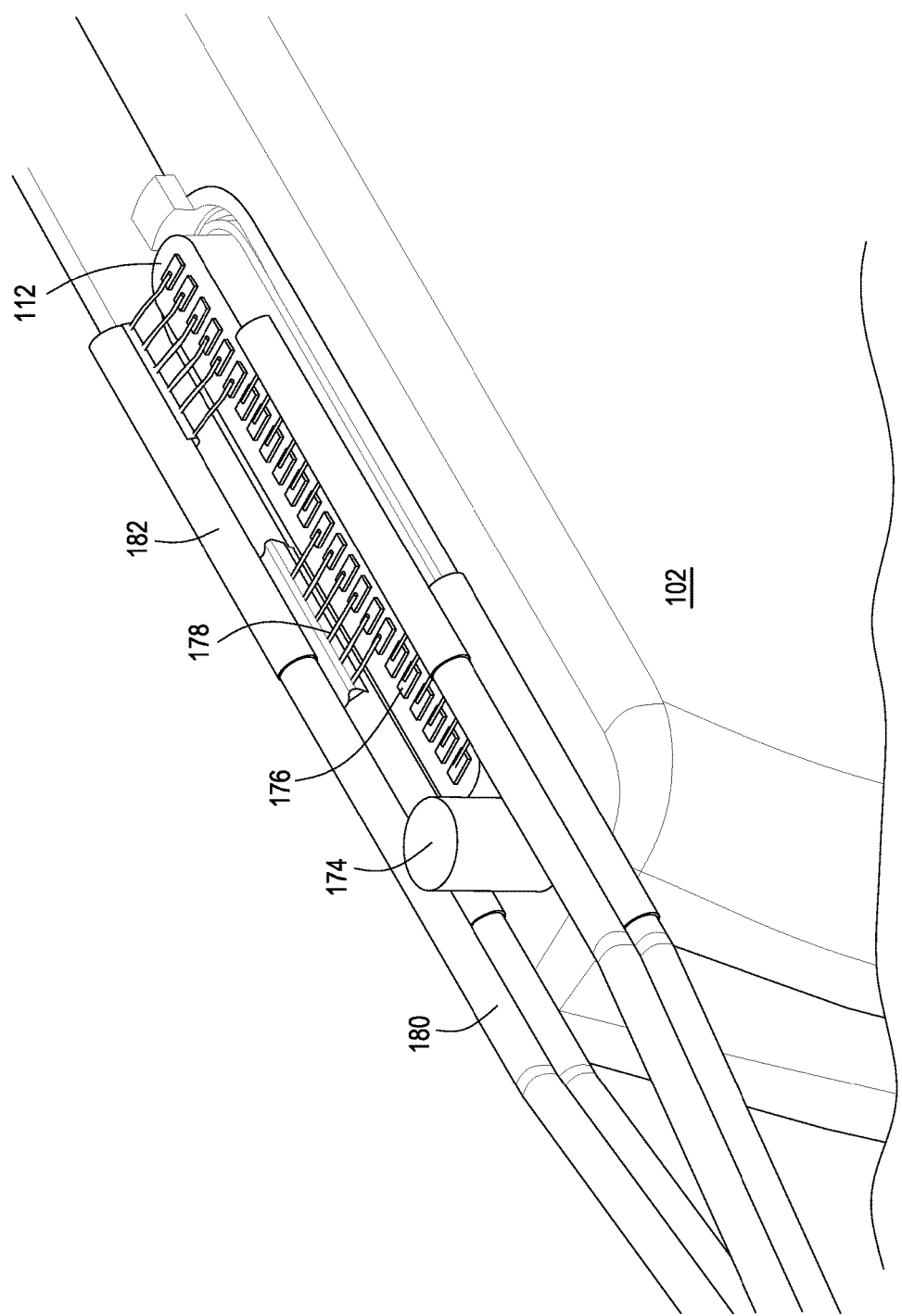
FIG. 9 shows a perspective view of the feedthrough and related conductors with the boot omitted for clarity.
Figure 10:
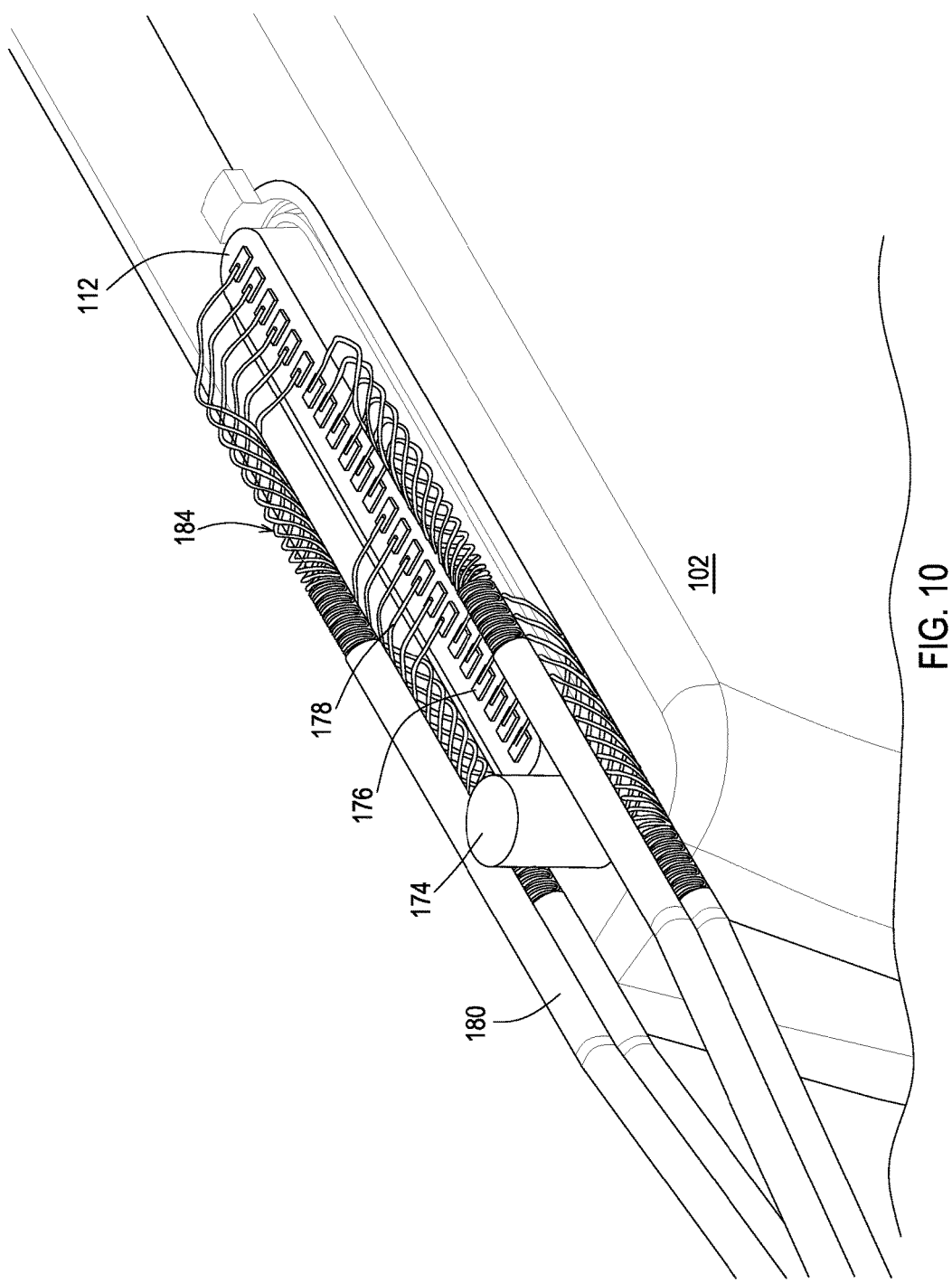
FIG. 10 shows a perspective view of the feedthrough and related conductors with the boot and cable sleeves omitted for clarity.
Figure 11:
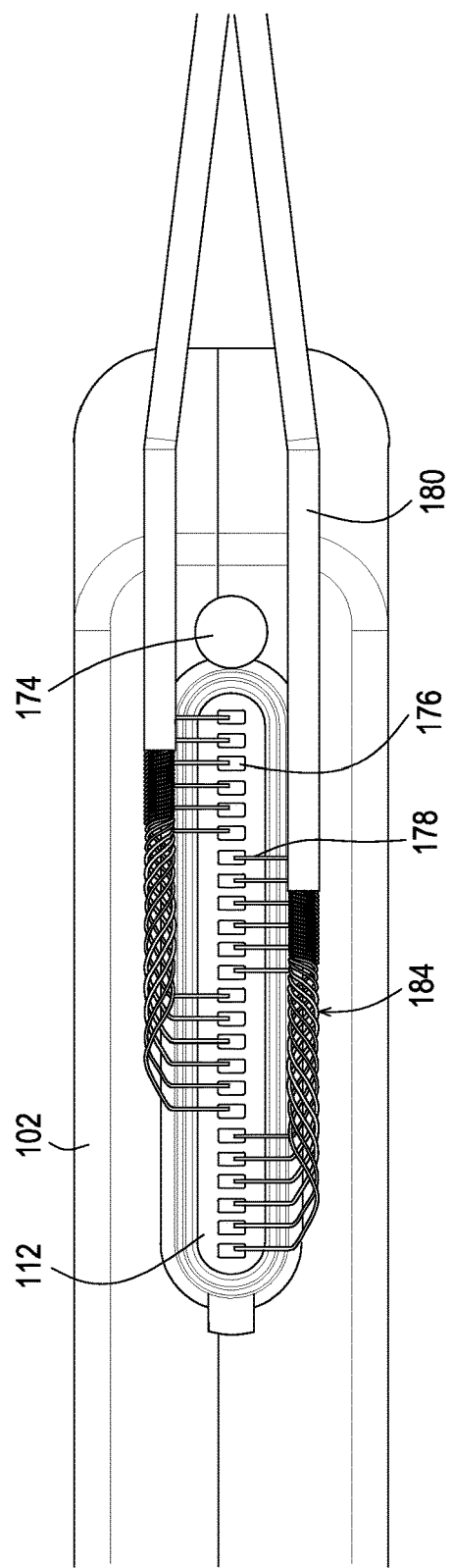
FIG. 11 shows a top view of the feedthrough and related conductors with the boot and cable sleeves omitted for clarity.
Figure 12:
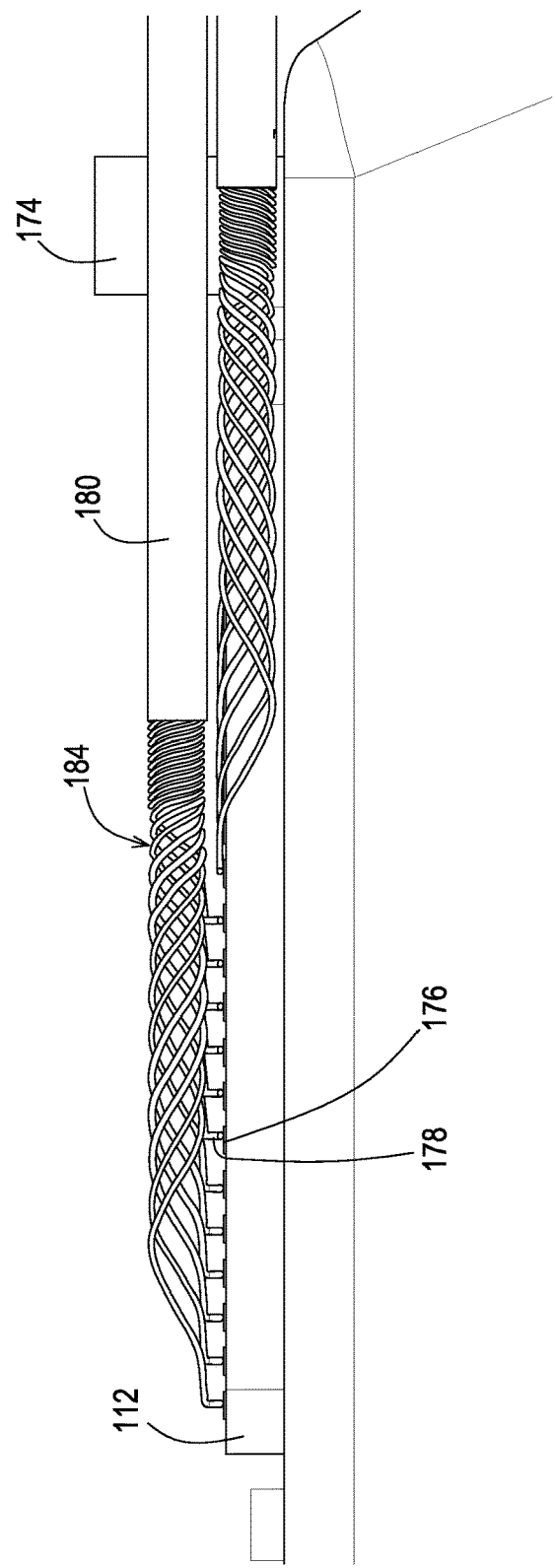
FIG. 12 shows a side view of the feedthrough and related conductors with the boot and cable sleeves omitted for clarity.

FIG. 9 shows the IMD 100 with the boot 104 removed to reveal the presence of individual elongated bodies 180. These elongated bodies 180 are in the form of cables carrying the individual conductors and may extend within the elongated body 106 to the one or more connectors 108 present at the distal end of the elongated body 106. Alternatively, each elongated body 180 may serve as the elongated body 106 by exiting the boot 104 and having a dedicated connector 108 at the distal end.

In the example of FIG. 9, each elongated body 180 includes six individual conductors, such as the conductors 168 shown in FIG. 7, where the conductor portion 178 of each conductor 168 exits the elongated body 180 to establish a bond to the corresponding contact pad 176. There are four elongated bodies 180 for a total of 24 conductors 168 and conductor portions 178 so that all of the contact pads 176 have a bonded conductor portion 178 and are available for use by the medical circuitry 116.

The proximal end of the elongated bodies 180 in this particular example of FIG. 9 are covered by cable sleeves 182. The sleeves 182 contain the individual conductors 168 while allowing the conductor portions 178 of the individual conductors 168 to exit the sleeve 182 in the direction of the feedthrough 112. In this example, the sleeves 182 terminate in proper alignment with the relevant section of the feedthrough 112 so that the conductor portions 178 are properly aligned with the corresponding contact pads 176 upon exiting the sleeve 182 in the direction of the feedthrough 112.

Where the sleeve 182 is formed over conductors 168 to properly orient and align them relative to the contact pads 176, then the conductor portions 178 may be attached to the contact pads 176 prior to placement of the boot 104. In that case, the boot 104 may be formed over the sleeves 182 without including an aperture 179. The boot 104 thereby holds the sleeves in position as opposed to the boot 104 directly holding each conductor 168 in position.

FIGS. 10-13 show various views of the IMD 100 with the boot 104 and the sleeves 182 removed. These views further reveal the coiled collection 184 of the individual conductors 168 from FIG. 7 that are present within each of the elongated bodies 180, the distal end 186 of the coiled collection 184 being shown in FIG. 13. The conductor portion 178 feeds into the collection of conductors 168 in a coiled manner for creating a compact collection of conductors contained within the elongated bodies 180. The coiled collection 184 may be beneficial to provide strain relief and the ability to stretch, align, and orient conductors 168 so that the conductor portions 178 align with the pads 176. The individual conductors 168 of the coiled collection 184 may be coated with an insulator such as ETFE or PTFE to prevent the individual conductors 168 from creating short circuits.

Various features of the illustrative embodiments are applicable in other embodiments independently of other features disclosed herein. For instance, the modular construction of the connector may be achieved by using contact modules but while not necessarily using other features. As one example, the modular connector may be constructed of contact modules while the attachment to the device utilizes a more conventional header, such as where the elongated body has significant length and is utilized as a lead extension. As another example, the modular connector may be constructed of contact modules that accommodate conventional canted spring connectors that may or may not float.

The direct connection of feedthrough conductors to electrical conductors of the elongated body may be achieved while not necessarily using other features. As one example, the direct connection of feed through conductors to electrical conductors may be present where a non-modular connector construction is used on the other end of the elongated body. As another example, the direct connection of feedthrough conductors and electrical conductors of the elongated body may be present where the connector has electrical contacts that are mounted within the connector in a fixed, non-floating manner.

The relatively thin electrical contacts with or without radial protrusions may be used while not necessarily using other features. As one example, these electrical contacts may be present within a non-modular connector construction that accepts these electrical contacts in a fixed or floating manner. As another example, these electrical contacts may be present where the attachment of the elongated body to the device utilizes a more conventional header.

Furthermore, the floating nature of the electrical contacts may be used while not necessarily using other features. For example, an electrical contact may float within a non-modular connector construction and the recessed area where the electrical contact is present provides freedom of movement in a radial direction. As another example, an electrical contact may float within a connector where the attachment of the elongated body to the device utilizes a more conventional header. As another example, an electrical contact may float within a connector while having a different design than being relatively thin with radial protrusions.

Embodiments provide an implantable medical device that includes a housing, circuitry within the housing, a feedthrough electrically connected to the circuitry and providing a plurality of feedthrough conductors externally of the housing, and an elongated body having a proximal end and a distal end. A plurality of conductors is located in the body, the plurality of conductors being electrically coupled to the feedthrough conductors in proximity to the proximal end of the body. A connector is attached to the distal end of the body, and the connector includes a plurality of adjacent contact modules, each contact module having at least one lead passageway. A plurality of contact isolators are included within the connector, with a contact isolator of the plurality being disposed within each of the at least one lead passageways of the corresponding contact modules of the plurality. A plurality of electrical contacts are included within the connector and are positioned within the lead passageway, with at least one electrical contact of the plurality being located axially between contact isolators, each of the plurality of contacts being in electrical communication with at least one of the conductors.

Each contact module of this implantable medical device embodiment may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts of this implantable medical device embodiment may include an extension that is present within a channel of the contact modules, extends along the channel of the plurality of modules toward the body and is electrically connected to one of the electrical conductors of the body. The connector may be encapsulated in a polymer. Each of the electrical contacts may surround the lead passageway and may include flexible radial protrusions. The plurality of adjacent contact modules may be fused. At least one contact isolator of the plurality may be co-molded with a corresponding contact module. Each contact isolator may be a ring made of a material such as silicone rubber.

Embodiments provide for an implantable medical device that includes a housing, circuitry within the housing, and a feedthrough electrically connected to the circuitry and providing at least one feedthrough conductor externally of the housing. A harness may be mounted to the housing, the harness including a boot attached to the housing about the feedthrough and receiving the at least one feedthrough conductor. At least one elongated body having a proximal end attached to the boot and having a distal end may be included in the harness. At least one conductor in the at least one body may be included in the harness, the at least one conductor being electrically coupled to the at least one feedthrough conductor. A connector attached to the distal end of the at least one body may be included in the harness, the connector comprising a lead passageway and at least one electrical contact within the lead passageway that is in electrical communication with the at least one conductor.

The feedthrough of this implantable medical device embodiment may provide a plurality of feedthrough conductors and the boot may receive the plurality of feedthrough conductors. The harness may further include a second elongated body having a proximal end attached to the boot and having a distal end. At least one conductor may be included in the second body, the at least one conductor being electrically coupled to at least one of the plurality of feedthrough conductors. A connector may be attached to the distal end of the second body, the connector including a lead passageway and at least one electrical contact within the lead passageway that is in electrical communication with the at least one conductor in the second body.

The connector of this implantable medical device embodiment may further include a plurality of adjacent contact modules, each contact module having at least one lead passageway. A plurality of contact isolators may be included within the connector, with a contact isolator of the plurality being disposed within each of the at least one lead passageways of the corresponding contact modules of the plurality. The plurality of electrical contacts may be positioned within the at least one lead passageway, with at least one electrical contact being located axially between contact isolators.

Each contact module of this implantable medical device embodiment has axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts of this implantable medical device embodiment may surround the lead passageway and may include flexible radial protrusions. The plurality of adjacent contact modules may be fused. Each contact isolator may be a ring and may be made of a material such as silicone rubber.

Embodiments provide an implantable medical device that includes a housing, circuitry within the housing, a feedthrough electrically connected to the circuitry and providing at least one feedthrough conductor externally of the housing, and a harness mounted to the housing. The harness may include an elongated body that has a proximal end and a distal end. At least one conductor is present in the body, the at least one conductor being electrically coupled to the at least one feedthrough conductor in proximity to the proximal end of the body. A connector may be included in the harness and be attached to the distal end of the body, the connector defining at least one lead passageway and comprising at least one electrical contact that is electrically coupled to the at least one feedthrough conductor. The at least one electrical contact may surround the lead passageway and have a thickness in an axial direction of 0.040 inches or less.

The electrical contact of this implantable medical device may float radially relative to the at least one lead passageway. The connector may further include a plurality of adjacent contact modules, each contact module having at least one lead passageway. A plurality of contact isolators may be present within the connector, with a contact isolator of the plurality being disposed within each of the at least one lead passageways of the corresponding contact modules of the plurality. The plurality of electrical contacts may be positioned within the at least one lead passageway, with at least one electrical contact being located axially between contact isolators. Each contact module may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts of this implantable medical device embodiment may include an extension that is present within a channel of the contact modules, extends along the channel of the plurality of contact modules toward the body, and is electrically connected to one of the electrical conductors of the body. The connector may be encapsulated in a polymer. Each of the electrical contacts may include flexible radial protrusions. The plurality of adjacent contact modules may be fused. Each contact isolator may be a ring. Each contact isolator may be made of silicone rubber.

Embodiments provide an implantable medical device that includes a housing, circuitry within the housing, a feedthrough electrically connected to the circuitry and providing at least one feedthrough conductor externally of the housing, and a harness mounted to the housing. The harness includes an elongated body that has a proximal end and a distal end. At least one conductor is present in the body, the at least one conductor being electrically coupled to the at least one feedthrough conductor in proximity to the proximal end of the body. A connector is included in the harness and is attached to the distal end of the body, the connector defining at least one lead passageway and comprising at least one electrical contact that is electrically coupled to the at least one feedthrough conductor. The at least one electrical contact is contained within the connector while having a radially floating relationship to the lead passageway.

The connector of this implantable medical device embodiment may further include a plurality of adjacent contact modules, each contact module having at least one lead passageway. A plurality of contact isolators may be included, with a contact isolator of the plurality being disposed within each of the at least one lead passageways of the corresponding contact modules of the plurality. The plurality of electrical contacts may be positioned within the at least one lead passageway of the adjacent contact modules, with at least one electrical contact being located axially between contact isolators.

Each contact module may have axial extensions spaced circumferentially on a first end, the plurality of contact modules being stacked so that an axial extension of one contact module fits into the lead passageway of an adjacent contact module. Each contact isolator of the plurality may be present between an abutment within the at least one lead passageway of the corresponding contact module and an end of the axial extensions of an adjacent contact module that are present within the at least one lead passageway of the corresponding contact module. Each electrical contact of the plurality may be disposed about the axial extensions of the plurality of contact modules.

Each of the electrical contacts may include an extension that is present within a channel of the contact modules extends along the channel of the plurality of modules toward the body and is electrically connected to one of the electrical conductors of the body. The connector may be encapsulated in a polymer. Each of the electrical contacts may surround the lead passageway and comprises flexible radial protrusions. The plurality of adjacent contact modules may be fused. Each contact isolator may be a ring and may be made of a material such as silicone rubber.

While embodiments have been particularly shown and described, it will be understood by those skilled in the art that various other changes in the form and details may be made therein without departing from the spirit and scope of the invention.

What is claimed is:

1. A method of constructing an implantable medical device, comprising:
   providing a housing;
   providing circuitry within the housing;
   providing a feedthrough electrically connected to the circuitry and providing at least one feedthrough conductor externally of the housing;
   mounting a harness to the housing, the harness comprising:
      an elongated body having a proximal end and a distal end;
      at least one conductor in the body, the at least one conductor being electrically coupled to the at least one feedthrough conductor in proximity to the proximal end of the body;
      a connector attached to the distal end of the body, the connector defining at least one lead passageway and comprising at least one electrical contact that is electrically coupled to the at least one feedthrough conductor, the at least one electrical contact surrounding the lead passageway and having a thickness in an axial direction of 0.040 inches or less.

2. The method of claim 1, wherein the at least one electrical contact floats radially relative to the at least one lead passageway.

3. The method of claim 1, wherein the connector further comprises:
- a plurality of adjacent contact modules, each contact module having at least one lead passageway;
- a plurality of contact isolators, with a contact isolator of the plurality being disposed within each of the at least one lead passageways of the corresponding contact modules of the plurality; and
- wherein the plurality of electrical contacts are positioned within the at least one lead passageway, with at least one electrical contact being located axially between contact isolators.

4. The method of claim 3, wherein each contact module has axial extensions spaced circumferentially on a first end, the plurality of contact modules being stacked so that an axial extension of one contact module fits into the lead passageway of an adjacent contact module,
- wherein each contact isolator of the plurality is present between an abutment within the at least one lead passageway of the corresponding contact module and an end of the axial extensions of an adjacent contact module that are present within the at least one lead passageway of the corresponding contact module, and
- wherein each electrical contact of the plurality is disposed about the axial extensions of the plurality of contact modules.

5. The method of claim 3, wherein each of the electrical contacts includes an extension that is present within a channel of the contact modules, extends along the channel of the plurality of contact modules toward the body, and is electrically connected to one of the electrical conductors of the body.

6. The method of claim 5, wherein the connector is encapsulated in a polymer.

7. The method of claim 3, wherein the plurality of adjacent contact modules are fused.

8. The method of claim 3, wherein each contact isolator is a ring.

9. The method of claim 3, wherein each contact isolator is made of silicone rubber.

10. The method of claim 1, wherein each of the electrical contacts comprises flexible radial protrusions.

* * * * *